(12) United States Patent
Dayton

(10) Patent No.: US 8,541,211 B2
(45) Date of Patent: *Sep. 24, 2013

(54) GENERATION OF TRIACYLGLYCEROLS

(75) Inventor: Christopher L. G. Dayton, Mount Kisco, NY (US)

(73) Assignee: Bunge Oils, Inc., St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 13/545,852

(22) Filed: Jul. 10, 2012

(65) Prior Publication Data

US 2013/0011889 A1    Jan. 10, 2013

Related U.S. Application Data

(63) Continuation of application No. 11/970,270, filed on Jan. 7, 2008, now Pat. No. 8,241,876.

(51) Int. Cl.
*C12P 7/64* (2006.01)
*C12N 9/14* (2006.01)
*C12N 9/20* (2006.01)
*C12P 1/00* (2006.01)
*C12N 9/00* (2006.01)

(52) U.S. Cl.
USPC ............. 435/134; 435/41; 435/183; 435/195; 435/198

(58) Field of Classification Search
None
See application file for complete search history.

(56) References Cited

U.S. PATENT DOCUMENTS

| | | | |
|---|---|---|---|
| 5,061,498 A | 10/1991 | Matsuzaki et al. |
| 5,204,002 A | 4/1993 | Belfort et al. |
| 5,264,367 A | 11/1993 | Aalrust et al. |
| 5,266,207 A | 11/1993 | Boye et al. |
| 5,342,521 A | 8/1994 | Bardot et al. |
| 5,532,163 A | 7/1996 | Yagi et al. |
| 5,558,781 A | 9/1996 | Buchold et al. |
| 6,001,626 A | 12/1999 | Kosugi et al. |
| 6,001,640 A | 12/1999 | Loeffler et al. |
| 6,103,505 A | 8/2000 | Clausen et al. |
| 6,127,137 A | 10/2000 | Hasida et al. |
| 6,140,094 A | 10/2000 | Loffler et al. |
| 6,143,545 A | 11/2000 | Clausen et al. |
| 6,146,869 A | 11/2000 | Harris et al. |
| 6,441,208 B2 | 8/2002 | Bijl et al. |
| 6,475,758 B2 | 11/2002 | Reaney |
| 6,489,154 B1 | 12/2002 | Berka et al. |
| 6,506,588 B2 | 1/2003 | Tsutsumi et al. |
| 6,509,182 B2 | 1/2003 | Tsutsumi |
| 6,511,837 B2 | 1/2003 | Tsutsumi |
| 6,514,739 B1 | 2/2003 | Udagawa et al. |
| 6,540,915 B2 | 4/2003 | Patil |
| 6,548,633 B1 | 4/2003 | Edwards et al. |
| 6,645,749 B2 | 11/2003 | Vind |
| 6,682,922 B2 | 1/2004 | Berka et al. |
| 6,695,967 B2 | 2/2004 | Bishop et al. |
| 6,727,373 B2 | 4/2004 | Bijl et al. |
| 6,733,814 B2 | 5/2004 | 't Hooft et al. |
| 6,759,225 B2 | 7/2004 | Udagawa et al. |
| 6,833,073 B2 | 12/2004 | Agarwal |
| 6,887,380 B2 | 5/2005 | Lee et al. |
| 6,887,408 B2 | 5/2005 | Yuan |
| 6,913,786 B2 | 7/2005 | Proulx et al. |
| 7,063,792 B2 | 6/2006 | Ozanne et al. |
| 7,091,003 B1 | 8/2006 | Harris et al. |
| 7,094,346 B2 | 8/2006 | Osenar et al. |
| 7,148,032 B2 | 12/2006 | Stringer et al. |
| 7,172,742 B2 | 2/2007 | Feng et al. |
| 7,186,344 B2 | 3/2007 | Hughes |
| 7,713,727 B2 | 5/2010 | Dayton et al. |
| 2002/0161066 A1 | 10/2002 | Remigy et al. |
| 2003/0000874 A1 | 1/2003 | Proulx et al. |
| 2003/0075506 A1 | 4/2003 | Tudhope |
| 2003/0090028 A1 | 5/2003 | Blase et al. |
| 2003/0121841 A1 | 7/2003 | Harttig et al. |
| 2003/0135971 A1 | 7/2003 | Liberman et al. |
| 2003/0144165 A1 | 7/2003 | Roggen |
| 2003/0186405 A1 | 10/2003 | Lee et al. |
| 2003/0203377 A1 | 10/2003 | Milne Edwards et al. |
| 2004/0005399 A1 | 1/2004 | Chakrabarti et al. |
| 2004/0005604 A1 | 1/2004 | Gramatikova et al. |
| 2004/0011723 A1 | 1/2004 | Bradford et al. |
| 2004/0101928 A1 | 5/2004 | Tsutsumi et al. |
| 2004/0110939 A1 | 6/2004 | Dumas Milne Edwards et al. |
| 2004/0159603 A1 | 8/2004 | Boulnois et al. |
| 2004/0179984 A1 | 9/2004 | Nagaraj et al. |
| 2004/0211726 A1 | 10/2004 | Baig et al. |
| 2004/0222148 A1 | 11/2004 | Yuan |
| 2004/0238439 A1 | 12/2004 | Oglesby |
| 2005/0009068 A1 | 1/2005 | Udagawa et al. |
| 2005/0059130 A1 | 3/2005 | Bojsen et al. |
| 2005/0061744 A1 | 3/2005 | Kearney et al. |
| 2005/0067340 A1 | 3/2005 | Broens et al. |

(Continued)

FOREIGN PATENT DOCUMENTS

| | | |
|---|---|---|
| EP | 654527 | 11/1994 |
| EP | 1624047 | 2/2006 |

(Continued)

OTHER PUBLICATIONS

De Maria L. et al., *Applied microbiology and biotechnology*, 2007, vol. 17, No. 2, pp. 290-300.

(Continued)

*Primary Examiner* — Chris R Tate
*Assistant Examiner* — Aaron J Kosar
(74) *Attorney, Agent, or Firm* — Jones Day

(57) ABSTRACT

A method is disclosed for the generation of triacylglycerols from gums that have been separated from an oil product. The gums are treated with an enzyme having PLC activity, which results in the formation of diacylglycerols and phosphates, and treated with an enzyme having PLA activity, which results in the formation of lyso-phospholipids and free fatty acids. The diacylglycerols and the free fatty acids from these two separate reactions then combine in the presence of the enzymes to generate new triacylglycerol molecules.

25 Claims, 8 Drawing Sheets

(56) References Cited

U.S. PATENT DOCUMENTS

| | | |
|---|---|---|
| 2005/0087491 A1 | 4/2005 | Hennige et al. |
| 2005/0106665 A9 | 5/2005 | Stringer et al. |
| 2005/0108789 A1 | 5/2005 | Gramatikova et al. |
| 2005/0118697 A1 | 6/2005 | Budolfsen et al. |
| 2005/0173330 A1 | 8/2005 | Osenar et al. |
| 2005/0284814 A1 | 12/2005 | Mairal et al. |
| 2006/0009633 A9 | 1/2006 | Dumas Milne Edwards et al. |
| 2006/0011544 A1 | 1/2006 | Sharma et al. |
| 2006/0030012 A1 | 2/2006 | Kellens et al. |
| 2006/0086654 A1 | 4/2006 | Voigt et al. |
| 2007/0009644 A1 | 1/2007 | Volland et al. |
| 2008/0182322 A1 | 7/2008 | Dayton et al. |
| 2009/0069587 A1 * | 3/2009 | Dayton et al. ............... 554/175 |
| 2009/0173689 A1 * | 7/2009 | Dayton ........................ 210/632 |

FOREIGN PATENT DOCUMENTS

| | | |
|---|---|---|
| JP | 63279751 | 11/1988 |
| JP | 02-153997 | 6/1990 |
| JP | 06306386 | 11/1994 |
| JP | 11-131089 | 5/1999 |
| JP | 11228986 | 8/1999 |
| JP | 2005328781 | 12/2005 |
| WO | WO 99/53001 | 10/1999 |
| WO | WO 01/68893 | 9/2001 |
| WO | WO 0224881 | 3/2002 |
| WO | WO 03070013 | 8/2003 |
| WO | WO 2004104193 | 12/2004 |
| WO | WO 2005063950 A1 * | 7/2005 |
| WO | WO 2005086900 | 9/2005 |
| WO | WO 2005/100579 | 10/2005 |

OTHER PUBLICATIONS

Clausen K., *European journal of lipid science and technology*, 2001, vol. 103, No. 6, pp. 333-340.

Mukherjee K. D., Schriftenreihe Des Bundesministers Fuer Ernaehrung, Landwirtschaft und Forsten. Reihe a, Anwandte Wissenschaft, Landwirtschaftsverlag, Muenster-Hiltrup, DE 1998, No. 469, pp. 102-114.

Ciofalo, Vince, Regulatory Toxicology and Pharmacology 2006, vol. 45, pp. 1-8.

Price, N.C. et al., *Fundamentals of Enzymology*, (3rd Edition 2003) Chapter 4, p. 118-153, Oxford University Press, Great Britain.

Ulbrich-Hofmann, R., *Enzymes in Lipid Modifications* (2000), pp. 218-262, Wiley-VCN GmbH & Co. KGaA, Weinheim.

E. H. Pryde, *Handbook of Soy Oil Processing* (1985), Chapter 2, pp. 13-31.

Dahlke, Klaus, Proceedings of the World Conference on Oilseed and Edible Oils Processing, vol. 1, pp. 53-59 (1998).

* cited by examiner

Phosphatidyl Choline

GENERATION OF TRIACYLGLYCEROLS

RELATED APPLICATIONS

This application is a continuation of and claims priority to U.S. patent application Ser. No. 11/970,270, filed Jan. 7, 2008, now U.S. Pat. No. 8,241,876 entitled "GENERATION OF TRIACYLGLYCEROLS FROM GUMS", the disclosure of which is incorporated herein by reference in its entirety.

BACKGROUND OF THE INVENTION

This invention relates to a method of generating triacylglycerols from gums that are recovered from an oil refining process. More particularly, this invention relates to an enzymatic process for the treatment of various phospholipids and lecithins (known collectively as "gums") from vegetable oils to produce or "generate" triacylglycerols (triglycerides or oils). The invention described herein is further work based on the inventions disclosed in U.S. patent application Ser. No. 11/668,921 filed Jan. 30, 2007 and U.S. patent application Ser. No. 11/853,339 filed Sep. 11, 2007, both of which are assigned to the common assignee and incorporated herein by reference.

Crude vegetable oils obtained from either pressing or solvent extraction methods are a complex mixture of triacylglycerols, phospholipids, sterols, tocopherols, free fatty acids, trace metals, and other minor compounds. It is desirable to remove the phospholipids, free fatty acids and trace metals in order to produce a quality salad oil with a bland taste, light color, and a long shelf life. Such removal of phospholipids, known as "gums," has been accomplished in the prior art by various methods including water degumming, acid degumming, caustic degumming, and enzyme degumming. Most of these degumming methods involve significant loss of oil along with the separated gums.

The aforementioned patent applications disclose methods of removing phospholipids from oil compositions by treating the oil compositions with both PLA enzymes and PLC enzymes. The treatment with the two enzymes can be either sequential or simultaneous. It was found that, surprisingly, the kinetics of the enzyme reactions proceed much more rapidly than expected when the two enzymes are used together than when either one is used separately. Further, it was found that when the two enzymes are used together the reactions proceed more rapidly than expected even if the reaction conditions are not optimized for at least one of the enzymes. It also was found that when the two enzymes are used together the reaction can proceed in less than about one hour, and can proceed as quickly as about thirty minutes.

The reactions of PLA and PLC enzymes with the oil compositions are expected to produce certain reaction byproducts that must be removed from the treated oil. These byproducts include phosphate bearing moieties cleaved from phospholipids by the PLC enzymes, free fatty acids cleaved from phospholipids by the PLA enzymes, and lyso-phospholipids resulting from the cleavage of the free fatty acid from the phospholipid. The lyso-phospholipids and any phosphate-bearing byproducts must be removed from the treated oil composition, and it is expected that the other aforementioned reaction byproducts would be removed along with the lyso-phospholipids in a heavy fraction known as "gums."

U.S. Pat. No. 5,061,498 relates to a method for reforming fats and oils which comprises treating the fats and oils containing partial glycerides with two or more different kinds of lipases which are different in a fatty acid specificity and/or position specificity in the presence of a small amount of water to obtain fats and oils containing partial glycerides in a low content. In the disclosed embodiment, lipase P is used because it will react at any of the three positions on a glycerol backbone. A desired fatty acid such as oleic acid can be added to a composition containing partial glycerides, and a lipase specific to that desired fatty acid such as lipase F is used. The presence of lipase F promotes the reaction of the preferred fatty acid over other fatty acids that may be present, and the presence of lipase P promotes the esterification of the preferred fatty acid at any location on the partial glycerides. The water concentration preferably is less than 1500 ppm, particularly 10 to 200 ppm.

It is an object of the present invention to provide a method for treating separated gums to obtain usable oil products that otherwise would be lost.

SUMMARY OF THE INVENTION

In furtherance of the work described in the two aforementioned patent applications, analyses were performed of gums that had been separated from PLA/PLC treated oils. It was expected that the gums would contain free fatty acids and diacylglycerols present in an amount proportional to the amount of phospholipids present in the original oil composition that had been reacted upon by the enzymes. Instead it was found that, surprisingly, there were substantially less free fatty acids and diacylglycerols than would have been expected by theory. From this surprising result it was concluded that the free fatty acids and the diacylglycerols that were the byproducts of the PLA and PLC reactions, respectively, with the phospholipids had reacted with one another in the presence of the PLA and PLC enzymes to form useful triacylglycerols, thus actually generating new oil molecules that had not existed before the PLA/PLC treatment process commenced. It thereby was discovered that the combination of PLA and PLC enzymes could be used to treat separated phospholipids, regardless of the method used to separate those phospholipids, to generate new triacylglycerol molecules.

Accordingly, the present invention relates to a method of generating triacylglycerols from oil gums, the method comprising (a) providing an oil composition containing a quantity of oil gums, said gums comprising phospholipids, (b) separating said oil gums from said oil composition to provide a first fraction substantially free of oil gums and a second fraction containing said separated oil gums, (c) treating said second fraction with one or more enzymes having PLA activity to generate free fatty acids, and (d) treating said second fraction with one or more enzymes having PLC activity to generate diacylglycerols, such that said fatty acids and said diacylglycerols react with one another in the presence of at least one of said enzymes to form triacylglycerols.

DETAILED DESCRIPTION OF THE INVENTION

Figure 1:
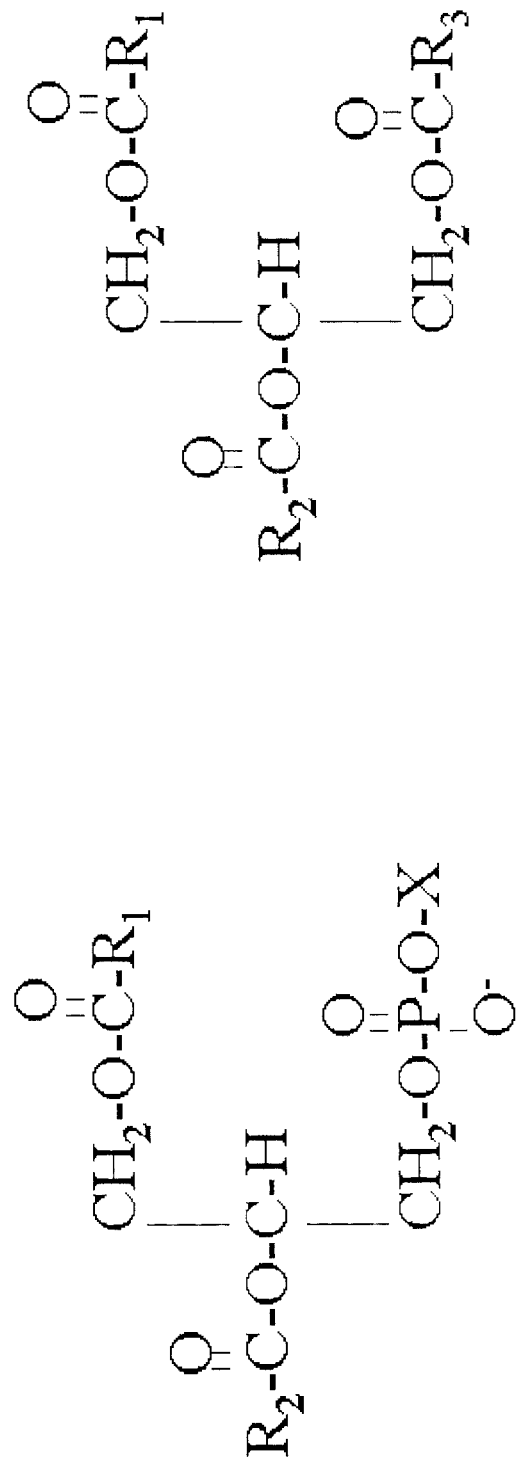
FIG. 1 is a drawing illustrating the configuration of phospholipid and triacylglycerol.
Figure 2:
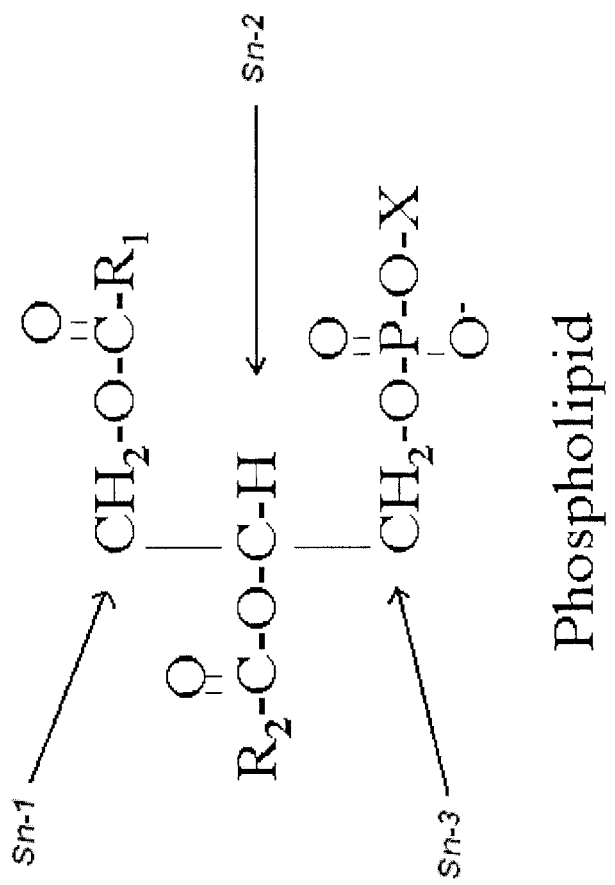
FIG. 2 is a drawing illustrating the three sterospecific locations of a phospholipid.

The removal of phospholipids generates almost all of the losses associated with the refining of vegetable oils. As illustrated in FIG. 1, phospholipids contain a phosphate group on one of the two ends of the glycerol backbone, whereas a triacylglycerol contains three fatty acids. In order to differentiate derivatives, the Sterospecific Numbering ("Sn") system is employed. FIG. 2 depicts the three sterospecific locations of a phospholipid.

The phosphate group of the phospholipid is "hydrophilic" or "water-loving," meaning that both the phosphate itself and the functional group X are attracted to water. The phospholipid's fatty acid chains R1 and R2 are "lipophilic" or "lipid-loving," meaning that they are attracted to lipids. Since the phospholipid molecule possesses both a hydrophilic functional group and lipophilic fatty acid chains, it is an excellent natural emulsifier. The emulsification properties of phospholipids will cause the removal of two phospholipid molecules and one molecule of triacylglycerol when the phospholipids are removed from vegetable oils.

Figure 3:
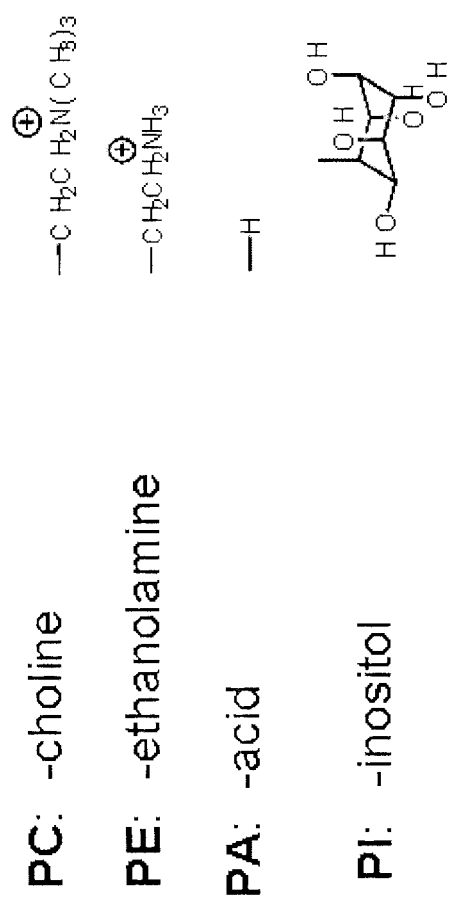
FIG. 3 is a drawing illustrating the structures of four common functional groups that can be attached to the phosphate moiety of a phospholipid.

The phospholipid's phosphate-containing functional group denoted in FIG. 1 as "X" determines the degree of its hydrophilic nature. The functional group X in FIG. 1 may be any of several of a variety of known types, a few of which are illustrated in FIG. 3.

Phospholipids containing the functional groups—choline and—ethanolamine have the greatest affinity for water, while the acids, acid salts (such as calcium, magnesium, and iron), and inositol have much lower affinities for water. Phosphatidic acid and the salts of phosphatidic acid are commonly known as "Non Hydratable Phospholipids" or NHPs. Phospholipids are commonly measured in oil as "phosphorous content" in parts per million. Table 1 sets forth the typical amounts of phospholipids present in the major oilseed crops, and the distribution of the various functional groups as a percentage of the phospholipids present in the oils. Table 2 sets forth the typical distribution of phospholipids present in lecithin (soybean gums). In Table 2, "as is" means the typical phospholipid composition removed from vegetable oil with the entrained oil (2 molecules of phospholipids and 1 molecule of oil), yielding an Acetone Insoluble content of 67%. "Normalized" means the phospholipid composition without any oil present, yielding an Acetone Insoluble content of 100%. Table 3 sets forth the molecular weights of the major types of phospholipids, lyso-phospholipids, and the corresponding non-lipid phospho-compounds. The term lyso-phospholipid as used in Table 3 and throughout this application means a phospholipid that has had one of its fatty acid groups cleaved by a lipase. The molecular weight of oleic acid is 282.48, and the molecular weight of the diacylglycerol wherein the fatty acids are present as oleic acid (C18:1) is 620.99.

TABLE 1

Typical phospholipid amounts and distributions for oils from common oilseeds.

|  | Soy Oil | Canola Oil | Sunflower Oil |
|---|---|---|---|
| P (ppm) | 400-1200 | 200-900 | 300-700 |
| PC (-choline) | 12%-46% | 25%-40% | 29%-52% |
| PE (-ethanolamine) | 8%-34% | 15%-25% | 17%-26% |
| PA (-acid) | 2%-21% | 10%-20% | 15%-30% |
| PI (-inositol) | 2%-15% | 2%-25% | 11%-22% |

TABLE 2

Typical phospholipid amounts and distributions for soybean gums

|  | Percentage "As-Is" | Percentage "Normalized" |
|---|---|---|
| Phosphatidyl Choline | 33.9 | 47.2 |
| Phosphatidyl Ethanolamine | 14.3 | 19.9 |
| Phosphatidyl Serine | 0.4 | 0.6 |
| Phosphatidyl Acid | 6.4 | 8.9 |
| Phosphatidyl Inositol | 16.8 | 23.4 |
| Total | 71.8 | 100.0 |

TABLE 3

Molecular weights of typical phospholipids and compounds

|  | Phospholipid Molecular Weight | lyso-Phospholipid Molecular Weight | Phospho-compound Molecular Weight |
|---|---|---|---|
| Choline - C18:1 | 786.15 | 521.67 | 183 |
| Ethanolamine - C18:1 | 744.00 | 479.52 | 141 |
| Serine - C18:1 | 787.03 | 522.55 | 184 |
| Acid - C18:1 | 721.90 | 457.42 | 98 |
| Inositol - C18:1 | 863.98 | 599.50 | 260 |

Phospholipids can be partially or totally removed from vegetable oils through several different processes, most commonly water degumming, acid degumming, caustic refining, and enzymatic degumming. The present invention of generating oils from gums can be used on gums derived from any of these processes; for purposes of illustration, enzyme degumming will be explained in more detail.

Enzymatic degumming, also known as "enzymatic refining," is used when the goal is the total removal of phospholipids from the oil. Generally, enzymatic degumming treatments of the prior art have been practiced on oils that have been degummed previously by one of the other methods, typically water degumming. For food applications, the enzyme degummed oil can be sequentially submitted to bleaching and deodorization, a process known in the industry as "physical refining." Enzymatic degumming provides a better oil yield than water, acid, or caustic degumming, with improved economic results.

Figure 4:
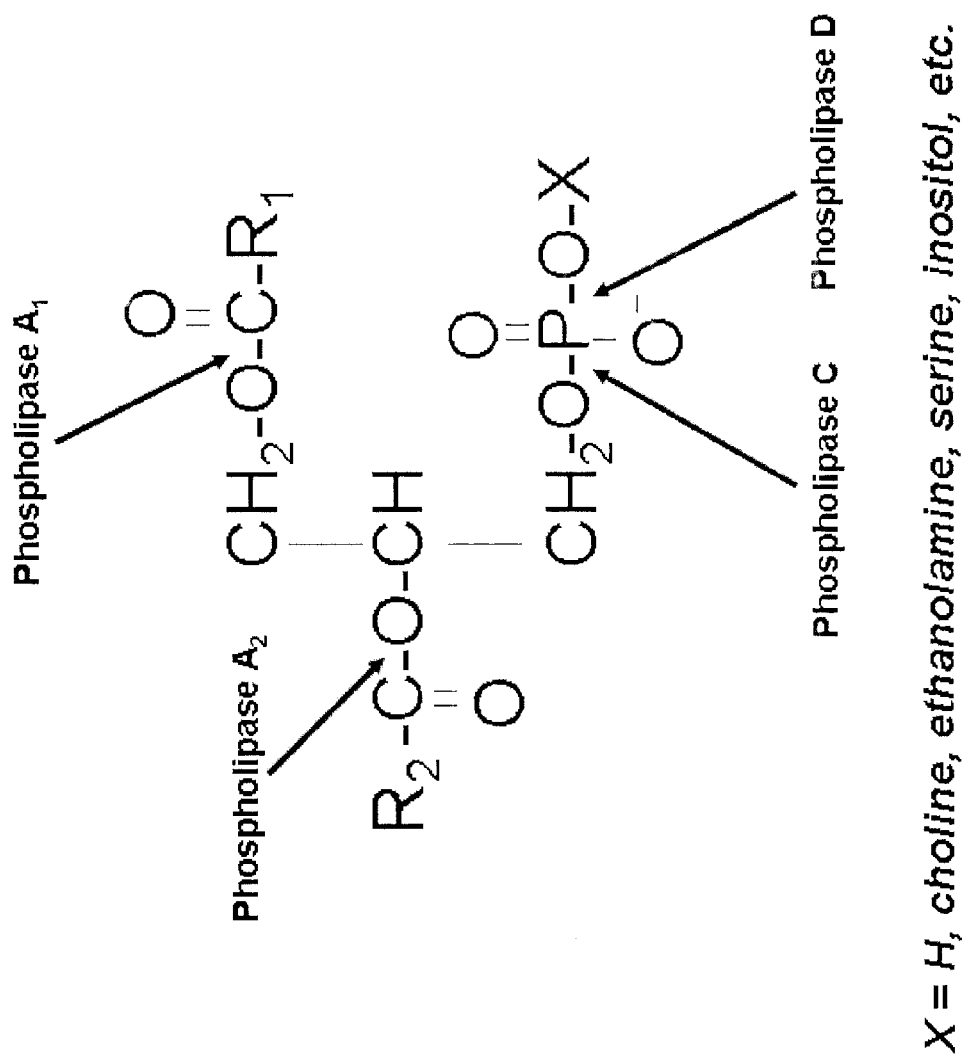
FIG. 4 is a drawing illustrating four different sites of enzyme attack on a phospholipid molecule.
Figure 5:
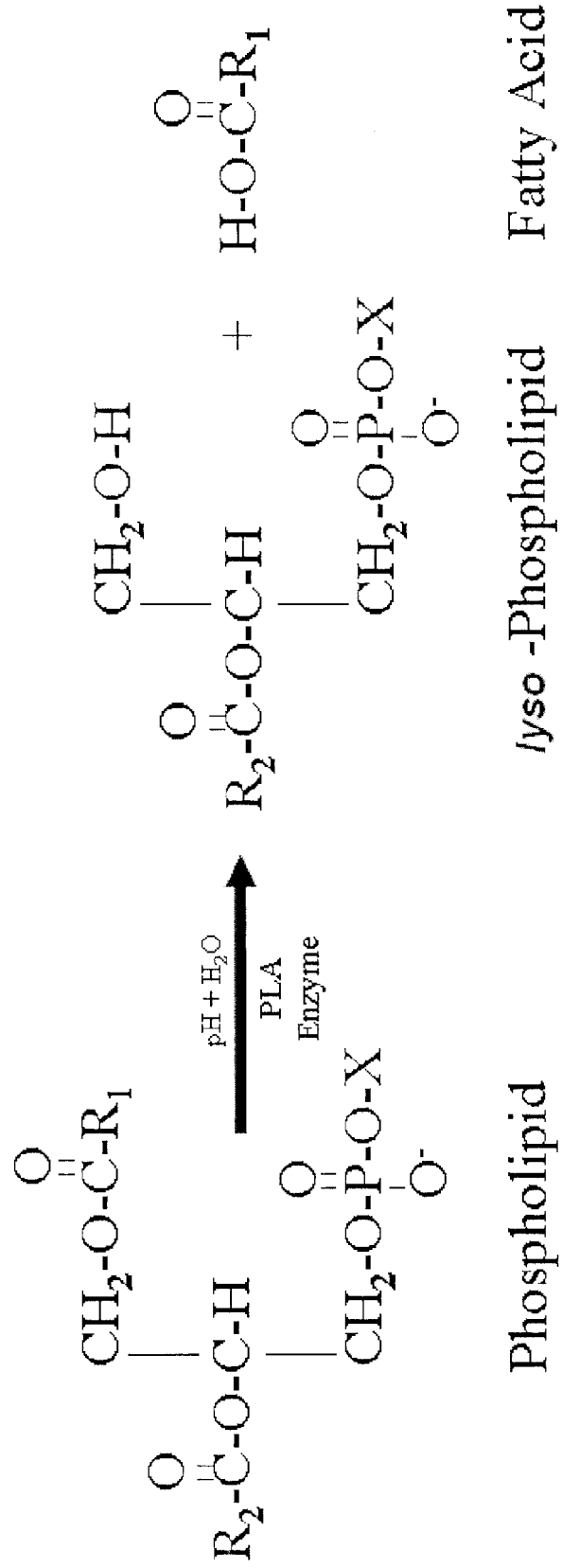
FIG. 5 is a drawing illustrating the reaction of a phospholipid in the presence of a PLA enzyme and water to produce a lyso-phospholipid and a fatty acid.

The enzymatic reaction changes the nature of the phospholipid, cleaving different functional groups of the molecule. The functional groups and breakdown products generally can be referred to as "fatty materials" and "phosphorous containing material." The enzyme reaction reduces the resulting phospholipids' emulsification properties, so that less oil is lost when the gums are separated from the oil, thus saving oil. Enzymes exhibiting activity with phospholipids are commonly called "phospholipases". The types of phospholipase are based on the position on the phospholipid molecule at which the enzyme reacts, and are known as PLAT, PLA2, PLC, and PLD. The positions on the phospholipid molecule at which the different types of phospholipases react are illustrated in FIG. 4. Phospholipase B is an additional enzyme known in the art. It removes the final fatty acid present either in the Sn-1 or Sn-2 position (FIG. 2) of a lyso-phospholipid. A summary of the various phospholipases and their reaction products is set forth in Table 4.

TABLE 4

|  | Fatty Material | Phosphorous Containing Material |
|---|---|---|
| Phospholipase A1 | fatty acid | lyso-phospholipid |
| Phospholipase A2 | fatty acid | 2 lyso-phospholipid |
| Phospholipase B | fatty acid | glycerophospholipid |
| Phospholipase C | diacylglycerol | Phosphate-containing head group |
| Phospholipase D | alcohol | phosphatidic acid |

Each type of phospholipase has its own rate of reaction and its own optimal reaction conditions in terms of pH, water concentration. and temperature. PLA when used alone generally requires a reaction time of at least about 4 hours, while PLC when used alone generally requires a reaction time of about one hour. It is known that enzymatic treatment should occur at a pH less than or equal to 8, in order to minimize undesirable oil saponification, but PLA has an optimum reaction pH of 4.5, while PLC has an optimum reaction pH of 7.0. Each enzyme also has different thermal tolerances. PLA enzymes will denature at about 50° C. while PLC enzymes will denature at about 65° C.

Sequences of amino acids with phospholipase activity are extensively reported in the literature and disclosed in patents, and some of those are reported to have activity on phospholipids present in vegetable oils. All this is known in the art.

One commercial PLA1 enzyme product with phospholipase activity is Novozymes' phospholipase A1 Lecitase® Ultra. As described in Novozymes' Application Sheet Oils & Fats#2002-185255-01 and 2002-05894-03, this product can be mixed with degummed oil with a 1-1.5% water citric acid-NaOH buffer at $4.5 < pH < 7.0$ and $40°$ C. $< T < 55°$ C. Under such conditions, the PLA1 selectively hydrolyzes the fatty acid opposite the phosphate functional group on the glycerol backbone to yield polar lyso-phospholipids and polar fatty acids. As illustrated in FIG. 4, the phospholipid molecule loses one hydrophobic functional group, i.e., the fatty acid, leaving the lyso-phospholipid, which now has a hydrophilic phosphate group and a hydrophilic alcohol group. Now with two hydrophilic sites, the lyso-phospholipid molecule is water soluble, and has lost its emulsification properties. Thus when the water phase is separated from the oil phase, the lyso-phospholipid is removed in the water phase, and does not remove any of the oils with it, while the cleaved fatty acid molecule from the phospholipid remains in the oil. In prior art processes this fatty acid molecule would be removed in a subsequent deodorization process. The PLA1 degumming process thus reduces refining losses by not removing any neutral oil with the lyso-phospholipids in the water phase, such that the only matter removed is the undesired lyso-phospholipid derived from the original phospholipid molecule.

The theoretical amount of fatty acids that can be generated by reacting gums with a PLA type enzyme can be calculated by determining the total amount of phospholipids in the gums, the amount of each type of phospholipid, and finally the change in molecular weight that occurs in the conversion of a phospholipid into a lyso-phospholipid for each type of phospholipid present. The percent phospholipid content can be calculated by multiplying the elemental phosphorous level measured in parts per million by 31 (molecular weight of phosphorous, 30.97) and dividing by 10000. The amounts of each type of phospholipid can be calculated by multiplying the total amount of gums by the normal distribution of each type of phospholipid known for the particular type of oil. Finally, the amount of liberated fatty acid can be determined from each type of phospholipid.

For example, for crude soybean oil containing 800 ppm of phosphorous with a "normalized" phospholipid distribution (Table 2), assuming the fatty acids attached to the phospholipids are oleic acid (C18:1), the fatty acids that are expected to be released can be calculated as follows:

First the percent of total phospholipid present is calculated.

Total Phospholipids=(800 ppm/1,000,000)×31×100=2.48 percent.

Then the amount of each type of phospholipid present is calculated.

Phosphatidyl Choline=(2.48×47.21)/100=1.17 percent

Phosphatidyl Ethanolamine=(2.48×19.92)/100=0.49 percent

Phosphatidyl Serine=(2.48×0.56)/100=0.01 percent

Phosphatidyl Inositol=(2.48×23.40)/100=0.58 percent

Phosphatidic Acid=(2.48×8.91)/100=0.22 percent

Finally, the amount of fatty acids liberated by the reaction of PLA with each type of phospholipid in the gums is determined by multiplying the amount of each type of phospholipid times the percentage of free fatty acid (FFA) released, the percentage of fatty acid being calculated as what remains after the amount of the lyso-phospholipid is subtracted away (cf. Table 3), as follows:

FFA from PC=1.17×(1−(521.67/786.15))=0.39 percent

FFA from PE=0.49×(1−(479.52/744.00))=0.18 percent

FFA from PS=0.01×(1−(522.56/787.03))=0.00 percent

FFA from PI=0.58×(1−(599.50/863.98))=0.18 percent

FFA from PA=(0.22×(1−(457.22/721.90))=0.08 percent

Total free fatty acids expected to be generated=0.83 percent

While enzymatic degumming offers significant advantages to oil processors, it also poses certain disadvantages. One disadvantage is that the reaction of the enzyme with the phospholipids can be slow and time consuming. In particular, the reaction of phospholipase A enzymes with phospholipids can take many hours, depending on reaction variables such as pH, temperature, relative concentrations, and mixing conditions. Such prolonged reaction times can have a significant negative impact on the overall economic value of enzymatic degumming processes. Because of the slowness of the PLA reaction, enzymatic degumming is typically carried out on oil compositions that have first been subjected to water degumming. Thus, the oil may be degummed twice to obtain a product that has a phosphorous level low enough for its intended purposes.

Figure 6:
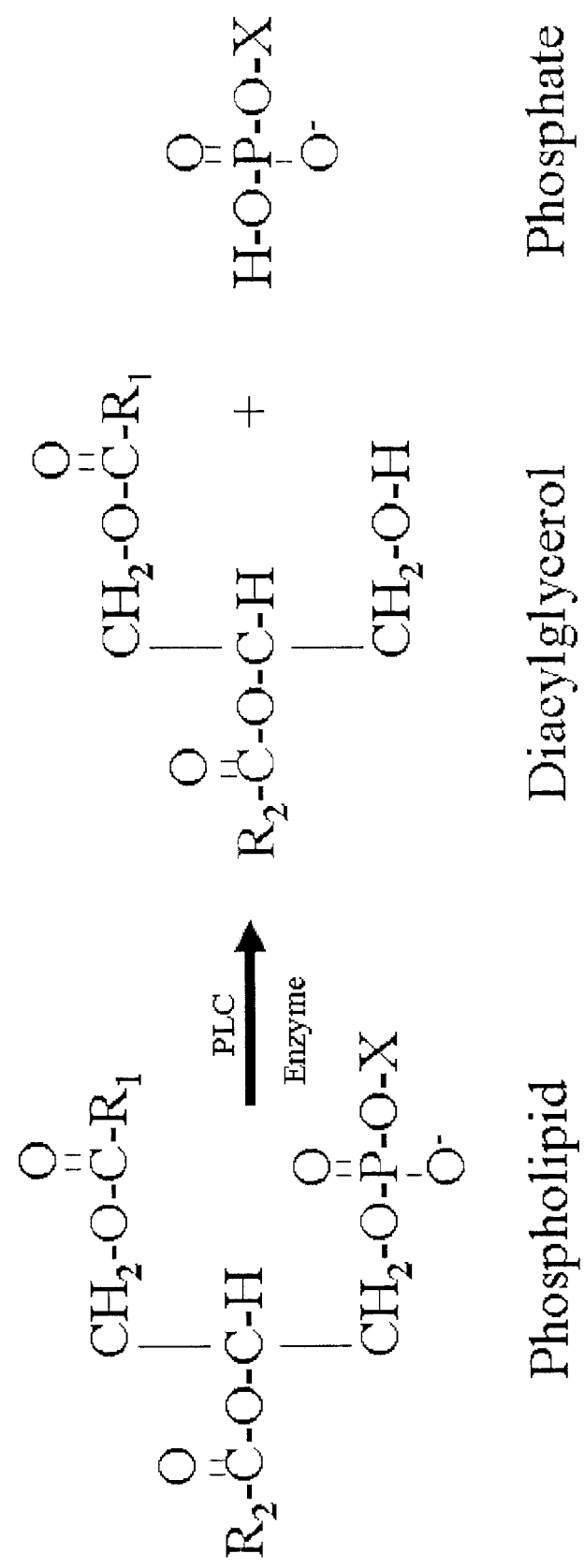
FIG. 6 is a drawing illustrating the reaction of a phospholipid in the presence of a PLC enzyme and water to produce a diacylglycerol and a phosphate.
Figure 7:
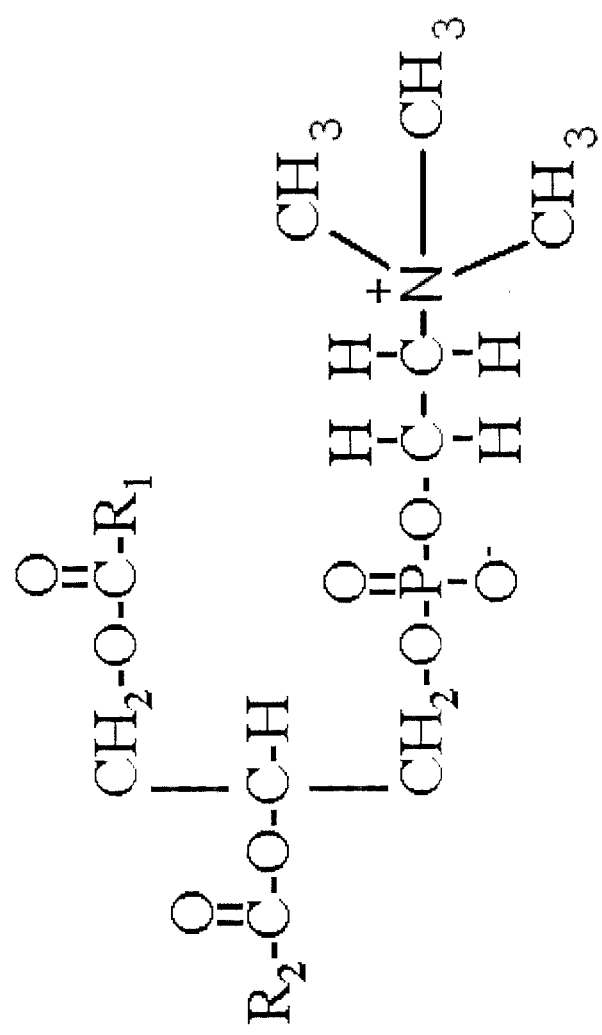
FIG. 7 is a drawing illustrating the structure of phosphatidyl choline.
Figure 8:
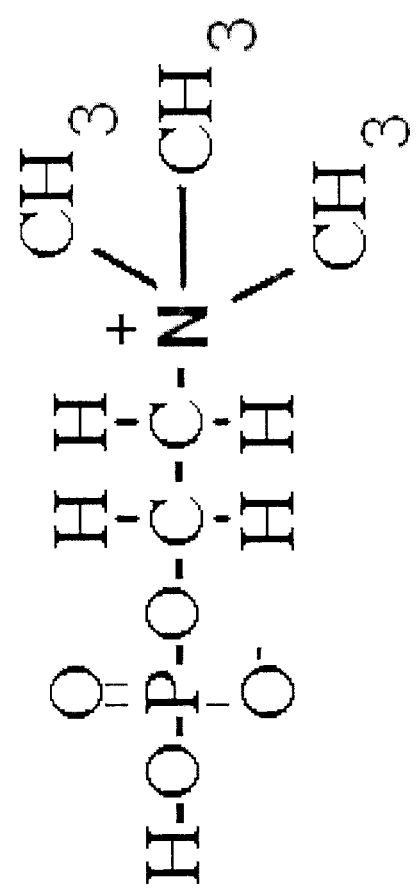
FIG. 8 is a drawing illustrating the structure of phosphocholine.

It is known in the art that PLC enzymes react with a phospholipid by selectively hydrolyzing the phosphate functional group, as shown in FIG. 6. The reaction yields a diacylglycerol ("DAG") and a phosphatidic group. The diacylglycerol molecule no longer has the phosphate functional group and does not need to be removed from the oil. For example, the reaction of Phosphatidyl Choline (PC), FIG. 7, with a PLC will yield a DAG and the phosphate functional group illustrated in FIG. 8, better known as phospho-choline or "C". The PLC degumming process reduces the refining loss by retaining the oil-soluble DAG, while removing only the water-soluble phosphate functional group. No neutral oil is lost when the water phase is removed because the phospholipid has been destroyed. However, the PLC enzyme does not react with all of the phospholipids present in the oil. Generally, PLC does not react with either phosphatidic acid (PA) or phosphatidic inositol (PI), illustrated in FIG. 3, although a PI-specific PLC, identified as PI-PLC, is known. Yet both PA and PI are non-hydratable phospholipids that remain in oil after water degumming. Thus oil that has been treated with PLC as the sole enzyme must be further treated such as with caustic or other enzymes to remove the residual gums.

The theoretical amount of diacylglycerols generated by the reaction of gums with a PLC type enzyme can be calculated by determining the percentage of phospholipids in the oil, the amount of each type of phospholipid in the type of oil, and finally the change in molecular weight that occurs upon conversion of a phospholipid into a DAG for each type of phospholipid present in the crude oil. The percent phospholipid content in the oil can be calculated by multiplying the elemental phosphorous level measured in parts per million by 31 (molecular weight of phosphorous, 30.97) and dividing by 10000. The individual phospholipids can be calculated by multiplying the total amount of gums times the normal distribution of each type of phospholipid. Finally, the amount of diacylglycerol can be determined that is the reaction product of each type of phospholipid.

For example, for crude soybean oil containing 800 ppm of phosphorous with a "normalized" phospholipid distribution (Table 2), assuming the fatty acids attached to the phospholipids are oleic acid (C18:1), the diacylglycerols that are expected to be released can be calculated as follows:

First the percent of each type of phospholipid is calculated, as described above.

Next the percent of each type of diacylglycerol (DAG) liberated by the reaction of PLC with the gums can be determined by multiplying the amount of each type of phospholipid by the percentage of diacylglycerols (Table 3), the amount of DAG being what remains after the amount of the phosphate group is subtracted away, as follows:

DAG from PC=1.17×(1−(165.10/786.15))=0.93 percent
DAG from PE=(0.49×(1−(123.10/744.00)=0.41 percent
DAG from PS=(0.01×(1−(166.08/787.03)=0.01 percent
DAG from PI=(0.58×(1−(243.00/863.98)=0.42 percent
DAG from PA=(0.22×(1−(100.92/721.90)=0.19 percent
Total diacylglycerols generated=1.96 percent The present invention relates to an enzymatic treatment of phospholipids and phosphorous-containing oil compositions to generate new triacylglycerol molecules. The inventor has found that, surprisingly, using a combination of phospholipases having PLA activity and PLC activity not only will cleave the specific "groups", but also re-combines a cleaved fatty acid (FA) from a PLA reaction and diacylglycerol (DAG) from a PLC reaction to produce a triglyceride, or oil. In particular, a Phospholipase A (PLA) reacts with a phospholipid molecule yielding a FA and lyso-lecithin, while a Phospholipase C (PLC) reacts with a different phospholipid molecule producing a DAG and a phospho-lecithin. The FA from the PLA reaction and the DAG from the PLC reaction then combine by esterification in the presence of one or more of the enzymes to produce a new triacylglycerol (TAG) molecule.

The present invention is particularly useful when used to further treat gums that have been removed from a crude oil by methods such as water refining, acid refining, or caustic refining, or by enzyme refining other than by a combination of PLA and PLC enzymes. It is believed that gums that had been separated by caustic refining would benefit by having the pH of the gums adjusted to about 8 or less before proceeding with the oil generation steps of the present invention.

Oils that can be treated in accordance with the present invention may include but are not limited to the following: canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, soybean oil, sunflower seed oil, tall oil, tsubaki oil, and vegetable oil, and any combination of the foregoing.

The phospholipase A enzyme used in the method of the present invention can be either a phospholipase A1 enzyme or a phospholipase A2 enzyme. The phospholipase C enzyme used in the present invention can be either a phospholipase C and/or an inositol specific phospholipase C. Many varieties of enzymes in the phospholipase A and phospholipase C families are available commercially; and it is contemplated that such enzymes and their equivalents will be suitable for use in the present invention.

In the method of the invention, the different phospholipases used together in an enzymatic degumming process of the present invention can be mixed together before being added to the oil to be treated. Alternatively, they can be added to the oil separately, either sequentially or simultaneously.

The degumming process of the present invention is carried out at a pH below about 8, preferable between about 3-7, and most preferably between about 4-5. The pH of the enzyme degumming process can be achieved by the addition of known buffers. Citric acid and sodium hydroxide are well known to be suited to this purpose. Other buffering agents can be used as needed to adjust the pH under specific reaction conditions.

The temperature of the enzymatic degumming process of the present invention can be in the range of about 40-80° C., preferably in the range of about 40-60° C., and more preferably in the range of about 45-55° C. It has been found that, surprisingly, under the methods of the present invention PLA degumming can proceed at a temperature above its own optimum of 45° C., and closer to the optimum operating temperature of PLC, without excessive denaturing.

After the oil generation process has been completed on the gums, and the newly generated oil has been separated from the gums, the newly generated oil can be subjected to further processing steps known in the art such as bleaching or deodorizing, as may be necessary or desirable depending on the end use for which the newly generated oil product is intended.

Various preferred embodiments of the invention are set forth in the examples below, along with control examples using conditions of the prior art. In each of the examples below, the overhead mixer was a Heidolph mixer model Elector KG with a flat blade paddle; operated at 90 rpm for normal agitation and 350 rpm for vigorous agitation. The centrifuge was a De Laval Gyro—Tester installed with "The Bowl Unit" for continuous separation. The centrifuge bowl was closed with the plug screws installed. Shear mixing was accomplished with an Ultra-Turrax homogenizer SD-45 with a G450 rotor stator at 10,000 rpm. The PLAT enzyme was Lecitase® Ultra (lot number LYN05007) sold by Novozymes A/S of Denmark. The PLC enzyme was Purifine™ (PLC lot number 90BU002A1 or 90BU004A1) sold by Verenium Corporation of San Diego, Calif. The amount of phospholipids remaining in the treated oil was measured as ppm P in accordance with the method of American Oil Chemists' Society Official Method Ca 20-99, "Analysis of Phosphorus in Oil by Inductively Coupled Plasma Optical Emission Spectroscopy." The Free Fatty Acid (FFA) was measured utilizing the American Oil Chemists' Society Official Method Ca 5a-40. Moisture was measured using American Oil Chemists' Society Official Method Ca 2c-25. Neutral oil was measured using the method set forth in the Appendix below. Acetone-insoluble mater including phospholipids was measured using American Oil Chemists' Society Official Method Ja 4-46. Acid Value was measured using American Oil Chemists' Society Official Method Ja 6-55. The P-31 NMR procedures and the Diacylglycerol (DAG) measurements by High Performance Liquid Chromatography with Evaporative Light Scattering Detector (HPLC-ELSD), were performed by the procedures as reported by Verenium Corporation (then known as Diversa Corporation), "Analytical Profiling of Small Scale Reactions of phospholipase-C mediated Vegetable Oil Degumming," at the American Oil Chemists Society 2007 meeting.

Of the following Examples, Examples 1-10 correspond directly to Examples 13, 14, 18, 23, 24, 27, 29, 31, 33, and 36 of the aforementioned U.S. patent application Ser. No. 11/853,339 filed Sep. 11, 2007, except that values of the free fatty acids (FFA) and diacylglycerols present in the enzyme degummed oil have been measured by the methods set forth above and are included herein.

Example 1

1999.1 grams of crude soybean oil containing 769.5 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 2.4 milliliters of 4 molar sodium hydroxide solution was added, and the mixture was shear mixed for 10 seconds. The citric acid and caustic formed a weak buffer with a pH of 5.0. With the temperature maintained at 40° C., 1.5008 grams of Verenium Purifine™ (PLC lipase lot number 90BU002A1) was added followed by 30 grams of de-ionized water and the entire mixture was shear mixed for 120 seconds. The oil mixture was agitated at normal speed for 60 minutes. With the temperature maintained at 40° C., 0.2132 grams of Novozymes' Lecitase® Ultra (PLA1 lipase lot number LYN05007) was added and the entire mixture was shear mixed for 120 seconds. The oil mixture was agitated at normal speed for 60 minutes at a temperature of 40° C. The enzyme treated oil was then centrifuged; and the separated oil and wet gums were collected. The residual phosphorous in the PLC then PLA1 sequential degummed oil was 6.5 ppm, FFA was 0.56%, and the DAG was 0.69%.

Example 2

2010.5 grams of crude soybean oil containing 785.1 ppm of phosphorous was cooled to 60° C. under normal agitation utilizing and overhead mixer. With the temperature maintained at 60° C., 1.5316 grams of Verenium's Purifine™ (PLC lipase lot number 90BU002A1) and 0.2073 grams Novozymes' Lecitase® Ultra (PLA1 lipase lot number LYN05007) were added followed by 30 grams of de-ionized water and the entire mixture was shear mixed for 45 seconds. The oil mixture was agitated at normal speed for 60 minutes at a temperature of 60° C. The enzyme treated oil was then centrifuged; and the separated oil and wet gums were collected. The residual phosphorous in the PLC and PLA1 combined enzyme mixture at neutral pH produced a degummed oil with a residual phosphorous of 109.6 ppm. The FFA was 0.61% and DAG was 0.74%.

Example 3

2005.3 grams of crude soybean oil containing 742.9 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 2.4 milliliters of 4 molar sodium hydroxide solution was added, and the mixture was shear mixed for 10 seconds. The citric acid and caustic formed a weak buffer with a pH of 5.0. With the temperature maintained at 60° C., 0.7491 grams of Verenium's Purifine™ (PLC lipase lot number 90BU002A1) was added followed by 60 grams of de-ionized water and the entire mixture was shear mixed for 45 seconds. The oil mixture was agitated at normal speed for 60 minutes. With the temperature maintained at 60° C., 0.1220 grams of Novozymes' Lecitase® Ultra (PLA1 lipase lot number LYN05007) was added and the entire mixture was shear mixed for 45 seconds. The oil mixture was agitated at normal speed for 60 minutes at a temperature of 60° C. The enzyme treated oil was then centrifuged; and the separated oil and wet gums were collected. The residual phosphorous in the PLC then PLA1 sequential degummed oil was 2.2 ppm. The FFA was found to be 0.58% and the DAG was 0.42%.

Example 4

2002.0 grams of crude soybean oil containing 747.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 2.2194 grams of Verenium's Purifine™ (PLC lipase lot number 90BU002A1) followed by 60 grams of de-ionized water were added and the entire mixture was shear mixed for 120 seconds. The oil mixture was agitated at normal speed for 15 minutes. With the temperature maintained at 60° C., 0.2198 grams of Novozymes' Lecitase® Ultra (PLA1 lipase lot number LYN05007) was added and the entire mixture was shear mixed for 120 seconds. The oil mixture was agitated at normal speed for 15 minutes at a temperature of 60° C. The enzyme treated oil was then centrifuged; and the separated oil and wet gums were collected. The residual phosphorous in the PLC and PLA1 sequential treated degummed oil had a residual phosphorous of 4.6 ppm. The FFA was 0.37% and the DAG was 0.42%.

Example 5

2000.8 grams of crude soybean oil containing 747.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 1.8 milliliters of 4 molar sodium hydroxide solution was added, and the mixture was shear mixed for 10 seconds. The citric acid and caustic formed a weak buffer with a pH of 4.5. With the temperature maintained at 50° C., 2.2500 grams of Verenium's Purifine™ (PLC lipase lot number 90BU002A1) was added and 0.2216 grams Novozymes' Lecitase® Ultra (PLA1 lipase lot number LYN05007) was added followed by 90 grams of de-ionized water and the entire mixture was shear mixed for 45 seconds. The oil mixture was agitated at normal speed for 120 minutes at a temperature of 50° C. The enzyme treated oil was then centrifuged; and the separated oil and wet gums were collected. The residual phosphorous in the PLC and PLA1 combined enzyme mixture produced a degummed oil with a residual phosphorous of 1.8 ppm. The FFA was 0.67% and the DAG was 0.40%.

Example 6

2010.0 grams of crude soybean oil containing 810.8 ppm of phosphorous was cooled to 50° C. under normal agitation utilizing and overhead mixer. With the temperature maintained at 50° C., 2.2608 grams of Verenium's Purifine™ (PLC lipase lot number 90BU002A1) followed by 30 grams of de-ionized water was added and the entire mixture was shear mixed for 60 seconds. The oil mixture was agitated at normal speed for 60 minutes. With the temperature maintained at 50° C., 0.1172 grams of Novozymes' Lecitase® Ultra (PLA1 lipase lot number LYN05007) was added and the entire mixture was shear mixed for 60 seconds. The oil mixture was agitated at normal speed for 60 minutes at a temperature of 50° C. The enzyme treated oil was then centrifuged; and the separated oil and wet gums were collected. The residual phosphorous in the PLC and PLA1 sequential treated degummed oil at a neutral pH had a residual phosphorous of 72.6 ppm. The FFA was 0.53% and the DAG was 1.03%.

Example 7

2006.3 grams of crude soybean oil containing 795.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 2.4 milliliters of 4 molar sodium hydroxide solution was added, and the mixture was shear mixed for 10 seconds. The citric acid and caustic formed a weak buffer with a pH of 5.0. With the temperature maintained at 50° C., 1.5373 grams of Verenium's Purifine™ (PLC lipase lot number 90BU002A1) and 0.1168 grams Novozymes' Lecitase® Ultra (PLA1 lipase lot number LYN05007) was added followed by 90 grams of de-ionized water and the entire mixture was shear mixed for 120 seconds. The oil mixture was agitated at normal speed for 30 minutes at a temperature of 50° C. The enzyme treated oil was then centrifuged; and the separated oil and wet gums were collected. The residual phosphorous in the PLC and PLA1 combined enzyme mixture at a pH of 5.0 produced a degummed oil with a residual phosphorous of 1.9 ppm. The FFA was 0.17% and the DAG was 0.42%.

Example 8

2003.6 grams of crude soybean oil containing 784.8 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 1.4603 grams of Verenium's Purifine™ (PLC lipase lot number 90BU002A1) and 0.1021 grams Novozymes' Lecitase® Ultra (PLA1 lipase lot number LYN05007) was added followed by 40 grams of de-ionized water and the entire mixture was shear mixed for 120 seconds. The oil mixture was agitated at normal speed for 120 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 10.7 ppm. The FFA was found to be 0.48% and the DAG was found to be 0.83%.

Example 9

2000.4 grams of crude soybean oil containing 697.7 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 1.508 grams of Verenium's Purifine™ (PLC lipase lot number 90BU002A1) and 0.1022 grams Novozymes' Lecitase® Ultra (PLA1 lipase lot number LYN05007) was added followed by 90 grams of de-ionized water and the entire mixture was shear mixed for 120 seconds. The oil mixture was agitated at normal speed for 30 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 2.2 ppm. The FFA was 0.20% and the DAG was 0.41%.

Example 10

1999 grams of crude soybean oil containing 695.1 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 1.5296 grams of Verenium's Purifine™ (PLC lipase lot number 90BU002A1) and 0.1241 grams Novozymes' Lecitase® Ultra (PLA1 lipase lot number LYN05007) was added followed by 90 grams of de-ionized water and the entire mixture was shear mixed for 120 seconds. The oil mixture was agitated at normal speed for 30 minutes at a temperature of 60° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 5.2 ppm. The FFA was found to be 0.36% and the DAG was 0.44%.

The focus of the inventions of the prior cited patent applications was to develop an enzymatic degumming process having reaction conditions resulting in the lowest possible residual phosphorous values with the least amount of processing aids, equipment, and time. Once the experiments were completed and all of the subsequent analytical testing completed, it was surprising to discover that the amount of fatty acids and diacylglycerols generated in the oils did not match the theoretical levels that should have been produced. Assuming that all of the PC and PE reacted with the PLC, then it would be expected that the DAG content would increase by approximately 1.16 to 1.35 percent, depending on the starting phospholipid content. Assuming that the PLA1 enzyme reacted with all of the phospholipids, then it would be expected that the FFA content would increase by approximately 0.77 to 0.83 percent, again depending on the starting phospholipid content. Additionally, if the PLC reacted with all of the PC and PE, then the expected FFA increase due to the remaining phospholipids reacting with the PLA would be roughly 0.53 to 0.59 percent for the above examples. The greatest increase in DAG was 0.63 percent with a fatty acid increase of 0.12 (Example 6), both well below the expected levels.

Analyses of the separated heavy phase or "gums" were performed on Examples 1-10 above in order to determine if the gums were hydrated and physically removed; the extent of each enzyme reaction; and if one enzyme predominately reacted over the other enzyme. Table 5 is a compilation of phospholipid composition/distribution analysis performed on the separated heavy phase via P-31 NMR, indicating the amount of unreacted phospholipid, the amount of lyso-phospholipids, and the amount of free phosphates, with all the amounts stated in terms of weight percent of the sample. (Note: No phospholipid data exists for example 6 due to microbial deterioration of the sample.)

and lyso-PE. The phospho-species of "C", "E", were also present in the recovered gums, as well as phospho-species "A", which was a surprise because it has been reported that PLC does not react with PA. Additionally, no phospho-inositol was detected. Comparing the distribution found in the gums to the original oil, 1.0 percent DAG and 0.40 percent FA were missing!

Example 2 was a simultaneous enzyme addition, at a pH of 7, with 1.5 percent water, and a 45 second shear mix. Both enzymes were in contact with the oil for 60 minutes at 60° C., thus the enzymes were in competition with one another. The centrifuged oil had a residual phosphorous of 109.6 ppm; DAG increased 0.34 percent, and the FFA increased 0.20 percent. The P31-NMR analysis of the collected gums detected only a small amount of PI present, and no PC, PE, or PA. Thus, all of the original phospholipids were reacted. Significant amounts of the lyso- and phospho-species were detected in the gums, except for "I". It was surprising to discover that the DAG increased only slightly compared with Example 1, but the amount of "C" and "E" were greater than were found in Example 1.

Example 3 was a sequential enzyme addition, at a pH of 5, with 3 percent water, and applied shear mixing for 45 seconds after the addition of each enzyme at 60° C. The PLC enzyme was in contact with the oil for 60 minutes before the PLA enzyme was added and both enzymes were allowed to react for an additional 60 minutes. The centrifuged oil contained 2.2 ppm phosphorous; the DAG essentially did not increase (0.40 to 0.42 percent) and the FFA increased only by 0.17 percent. Comparing the collected gums from Example 3 to

TABLE 5

| Ex | PC | PE | PI | PA | l-PC | l-PE | l-PI | l-PA | "C" | "E" | "I" | "A" |
|----|------|------|------|------|-------|------|------|-------|------|------|------|------|
| 1  | 0.00 | 0.00 | 1.73 | 0.00 | 1.81  | 0.22 | 5.71 | 7.01  | 3.82 | 2.75 | 0.00 | 0.81 |
| 2  | 0.00 | 0.00 | 0.19 | 0.00 | 1.43  | 2.27 | 6.11 | 4.22  | 4.56 | 3.40 | 0.00 | 0.82 |
| 3  | 1.02 | 0.00 | 2.77 | 0.00 | 9.55  | 0.21 | 8.30 | 13.25 | 2.47 | 1.34 | 0.00 | 0.50 |
| 4  | 0.99 | 0.00 | 4.76 | 0.95 | 5.28  | 0.32 | 5.93 | 10.81 | 3.73 | 1.81 | 0.00 | 0.49 |
| 5  | 1.62 | 0.00 | 3.35 | 0.78 | 12.29 | 0.21 | 8.28 | 11.91 | 1.49 | 0.89 | 0.00 | 0.46 |
| 6  | —    | —    | —    | —    | —     | —    | —    | —     | —    | —    | —    | —    |
| 7  | 0.00 | 0.16 | 1.10 | 0.00 | 1.32  | 0.38 | 5.35 | 1.24  | 3.56 | 2.95 | 0.00 | 0.93 |
| 8  | 0.00 | 0.15 | 1.08 | 0.00 | 1.60  | 0.67 | 6.37 | 1.98  | 4.37 | 3.57 | 0.00 | 1.33 |
| 9  | 0.08 | 0.00 | 3.03 | 0.00 | 1.93  | 0.08 | 5.07 | 10.80 | 3.85 | 2.58 | 0.00 | 0.84 |
| 10 | 2.09 | 0.00 | 4.26 | 0.00 | 7.22  | 0.24 | 6.90 | 12.81 | 2.06 | 1.14 | 0.00 | 0.49 |

Example 1 was a sequential addition of enzymes at a pH of 5 allowing the PC and PE to react first with the PLC enzyme, and then allowing the PI, PA, and any remaining PC and PE to react with the PLAT enzyme. The PLC enzyme was in contact with the oil for 60 minutes at 40° C. before the PLA enzyme was added, thus allowing the enzyme to react with all of the PC and PE present in the oil without competition with the PLA enzyme. After the initial PLC reaction, the PLA was added such that the PLA could hydrolyze the remaining phospholipids present in the oil. The residual phosphorous, as noted above, was successfully reduced to 6.5 ppm. The starting oil had a DAG content of 0.40 percent and a FFA of 0.41 percent compared to the final oil containing 0.69 percent DAG and a FFA of 0.56 percent. If both of the enzymes reacted with the specific phospholipids, then the DAG should have been increased by 1.29 percent to 1.69 percent and the FFA should have increased by 0.55 percent to 0.96 percent. The actual DAG was found to have only increased by 0.29 percent and the FA only increased by 0.15 percent. P-31 NMR analysis of the gums showed all of the original phospholipids were hydrolyzed except the PI. Significant amounts of lyso-PI and lyso-PA were present with minor amounts of lyso-PC Example 2, a large increase in the lyso-species was present while the phospho-species were all depressed. These results indicate that at these conditions, the PLA reaction dominated over the PLC reaction, even though PLC was added first. The amount of DAG and FFA should have been far greater than was present in the finished oil based on the disappearance of the starting phospholipids and the appearance of the reaction products!

Example 4 was a sequential enzyme addition, at a pH of 4.5, 3 percent water, and shear mixing for 120 seconds after the addition of each enzyme at 60° C. The PLC enzyme was in contact with the oil for 15 minutes before the PLA enzyme was added and both enzymes were allowed to react for an additional 15 minutes. The centrifuged oil contained only 4.6 ppm phosphorous, the DAG increased only by 0.02 percent, while the FFA went down by 0.04 percent. An evaluation of the collected gums showed some PC, PA, and PI that were not hydrolyzed. The lyso- and phospho-species were not as high as were found in Example 3, but were still elevated considering the limited contact with the enzymes.

Example 5 was a simultaneous enzyme addition, at a pH of 4.5, with 4.5 percent water, and a 45 second shear mix. Both enzymes were in contact with the oil for 120 minutes at 50° C., thus the enzymes were in competition with one another during the entire reaction. The centrifuged oil had a residual phosphorous of 1.8 ppm; DAG did not increase at all, and the FFA increased 0.26 percent. The analyzed gums showed a large increase in the amount of lyso-species and a decrease in phospho-species compared to the previous four examples, indicating that PLA is dominating over PLC in the reaction mixture.

Example 6 was a sequential addition of enzymes at a pH of 7. The PLC enzyme was in contact with the oil for 60 minutes at 50° C. before the PLA enzyme was added, thus allowing the enzyme to react with all of the PC and PE present in the oil without competition with the PLA enzyme. After the initial PLC reaction, the PLA was added such that the PLA could hydrolyze the remaining phospholipids present in the oil. The residual phosphorous, as reported previously, was only reduced to 72.6 ppm. The starting oil had a DAG content of 0.40 percent and a FFA of 0.41 percent, while the final oil contained 1.03 percent DAG and a FFA of 0.53 percent. If both of the enzymes reacted with the specific phospholipids, then the DAG should have been increased by 1.36 percent to 1.76 percent and the FFA should have increased by 0.57 percent to a total of 0.98 percent. The actual DAG was found to have increased by 0.63 percent and the FFA only increased by 0.12 percent. No P-31 NMR analysis of the gums was available due to microbial deterioration of the sample.

Example 7 was a simultaneous enzyme addition. The enzymes were in contact with the oil sample for a total of only 30 minutes at a pH of 5 with 4.5 percent water, and at a temperature of 50° C. The residual phosphorous in the oil was only 1.9 ppm. The lyso-species were all depressed, especially the lyso-PC. The phospho-species were all twice as much as were found in the Example 5 gum analysis, indicating that under these conditions the PLC dominated over the PLA. However, the DAG content essentially did not increase (0.40 to 0.41 percent) compared to the starting oil and the FFA did not increase to the expected total of 0.98 percent, but actually decreased by 0.24 percent for a total FFA of 0.17 percent!

Example 8 was a simultaneous enzyme addition, at a pH of 4.5, with 2 percent water, and a 120 second shear mix. Both enzymes were in contact with the oil for 120 minutes at 40° C., thus the enzymes were in competition with one another during the entire reaction. The centrifuged oil had a residual phosphorous of 13.3 ppm; DAG increased by 0.43, and the FFA increased 0.07 percent. The lyso-species were all depressed while phospho-species were still higher than those in Example 7.

Example 9 was similar to the reaction in Example 8, but instead of 2 percent water, 4.5 percent water was added in the simultaneous enzyme reaction and the enzyme contact time was 30 minutes instead of 120 minutes. The residual phosphorous in the oil was 2.2 ppm. The amount of DAG present in the oil essentially remained the same as the starting oil while the FFA decreased from the initial oil by 0.21 percent. The low residual phosphorous level and elevated amounts of all the lyso-species, especially the lyso-PA, indicated high PLA enzyme activity. From this it was expected that a very large amount of FFA should have been generated in the reaction process. The phospho-species were slightly depressed in comparison to Example 8, but the DAG should have been significantly higher according to the amounts of phospho-species present in the gums.

Example 10 was carried out with a simultaneous enzyme addition, at a pH of 4.5, with 4.5 percent water, and a shear mix of 120 seconds. The enzymes were in contact with the oil for 30 minutes at 60° C. The residual phosphorous in the oil was 5.2 ppm. The amount of DAG present in the oil essentially remained the same as the starting oil (0.40 to 0.44) while the FFA decreased from the initial oil by 0.05 percent; while maintaining roughly the same amount of by-products in the gums as example 3. The reaction conditions of examples 3 and 10 were different, yet the results in terms of resulting phospho-species, DAG and FFA were about the same, indicating that the reaction is very robust in forming TAG.

Table 6 below is a summary of the initial phosphorous, DAG, and FFA of the starting oils for each of examples 1-10 above, the theoretical amount of DAG and FFA that would have been present in the treated oil if all the phospholipids in the starting oil had reacted with the enzymes, and the measured amounts of phosphorous, DAG and FFA in the treated oil.

TABLE 6

| Example | Starting Oil | | | Theoretical Amounts in Treated Oil | | Measured Amounts in Treated Oil | | |
|---|---|---|---|---|---|---|---|---|
| | Phos (ppm) | DAG (%) | FFA (%) | DAG* (%) | FFA** (%) | Phos (ppm) | DAG (%) | FFA (%) |
| 1 | 769.5 | 0.40 | 0.41 | 1.69 | 0.96 | 6.5 | 0.69 | 0.56 |
| 2 | 785.1 | 0.40 | 0.41 | 1.71 | 0.97 | 109.6 | 0.74 | 0.61 |
| 3 | 742.9 | 0.40 | 0.41 | 1.64 | 0.94 | 2.2 | 0.42 | 0.58 |
| 4 | 747.3 | 0.40 | 0.41 | 1.65 | 0.94 | 4.6 | 0.42 | 0.37 |
| 5 | 747.3 | 0.40 | 0.41 | 1.65 | 0.94 | 1.8 | 0.40 | 0.67 |
| 6 | 810.8 | 0.40 | 0.41 | 1.76 | 0.98 | 72.6 | 1.03 | 0.53 |
| 7 | 795.3 | 0.40 | 0.41 | 1.73 | 0.98 | 1.9 | 0.42 | 0.17 |
| 8 | 783.9 | 0.40 | 0.41 | 1.71 | 0.97 | 13.3 | 0.83 | 0.48 |
| 9 | 697.7 | 0.40 | 0.41 | 1.57 | 0.91 | 2.2 | 0.41 | 0.20 |
| 10 | 695.1 | 0.40 | 0.41 | 1.56 | 0.90 | 5.2 | 0.44 | 0.36 |

*Theoretical DAG only includes generation from phosphatidyl choline and phosphatidyl ethanolamine.
**Theoretical FFA only includes the generation from phosphatidyl serine, phosphatidyl inositol, and phosphatidic acid.

P-31 NMR analysis of the gums confirmed that the gums were not being hydrated and physically separated from the oil as in the "normal" water and/or acid degumming process, but were hydrolyzed by the PLC and PLA enzymes. The analysis confirmed the formation of the cleaved phospho-species and creation of lyso-lecithins (Table 5). It did not, however, explain why the levels of DAG and FFA were depressed in the treated oils. No information in the prior art could be found to describe why significant amounts of DAG and FFA appeared to be missing.

U.S. patent application Ser. No. 11/668,921, and U.S. patent application Ser. No. 11/853,339 of Dayton et al. disclose an enzymatic method for removing various phospholipids from vegetable oils to produce a degummed oil with a combination of enzymes in which the reaction period can be one hour or less. The inventors reveal a synergistic effect between PLC enzymes and PLA enzymes, improving the kinetics of the reaction from two to six hours when the enzymes are used alone to one hour or even less when the two enzymes are used together.

The present invention is based on the unexpectedly low levels of DAG and FFA found in these subsequent analyses of these treated oils. Based on these results, the invention herein lies in the discovery that PLA and PLC apparently interact synergistically in a matrix of lipids containing phospholipids and their PLA/PLC hydrolysis byproducts to produce triacylglycerols. Without wishing to be bound by theory, it is believed that the cleaved diacylglycerol byproducts from the PLC hydrolysis and the cleaved fatty acids from the PLA hydrolysis combine under the enzymatic degumming process conditions to create new triacylglycerols. It is theorized that the proximity or the orientation, or both, of the two enzymes allows the formation of the triacylglycerols during the release of both the diacylglycerols and fatty acids in the water phase of the reaction.

An additional series of examples was performed on gums produced from crude soybean oil utilizing the traditional water degumming process as described in the prior art earlier. The wet gums were obtained directly from an industrial water degumming process. The wet gums were utilized as a raw material to eliminate the majority of the triacylglycerols present in oil while maintaining all the other minor components that may be present in the "typical" degumming matrix. The P-31 NMR analysis of the gums detected only the phosphatidyl species and none of the lyso- or phospho-species. The phospholipid compositional data is listed below in Table 7. The diacylglycerol content of the gums obtained from the industrial water degumming process was 1.5 percent.

Two control examples were conducted at each of the enzyme's optimum reaction conditions to determine the base case for further analysis of the experiments. The first control was at a neutral pH for the phospholipase C enzyme and the second experiment was conducted at a pH of 4.5, the optimum for the phospholipase A enzyme.

Example 11

Control: Phospholipase C (PLC) at neutral pH-50 grams of wet soybean gums were added to a 500 ml round bottom flask. 10 grams of Verenium's Purifine™ (PLC lipase lot number 90BU004A1) were added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzyme were heated to 45° C. under continuous agitation. The system was maintained for eight hours. The apparatus was then disassembled and the hydrolyzed gums were collected. The gums were placed in a centrifuge tube and centrifuged for 15 minutes at 5000 rpm to separate the light phase ("oil") from the heavy phase ("gums").

The DAG content of the recovered oil was determined to be 32.6 percent, compared to a starting DAG of 1.5 percent, for a difference of 31.1 percent. The large increase in DAG content is consistent with a PLC reaction, in which the DAG does not react further. The phospholipid profile obtained by P31-NMR analysis of the heavy phase confirmed that the phosphatidyl groups had been hydrolyzed to the phospho-groups. Unexpectedly, a small amount of "I" was detected, as well as small amounts of all the lyso-groups. Thus the PLC does possess some PLA activity under the reaction conditions of this example.

Example 12

Control: Phospholipase A (PLA) at pH 4.5—50 grams of wet soybean gums were added to a 500 ml round bottom flask. 2.0 grams of 50% w/w solution of citric acid was added and mixed for 5 minutes. Then 1.8 milliliters of 4 molar sodium hydroxide solution was added, and the mixture was mixed for an additional 5 minutes. The citric acid and caustic formed a weak buffer with a pH of 4.5. 2 grams of Novozymes' Lecitase® (PLAT lipase lot number LYN05007) was added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzymes were heated to 45° C. under continuous agitation. The system was maintained for eight hours. The apparatus was then disassembled and the hydrolyzed gums were collected. The gums were placed in a centrifuge tube and centrifuged for 15 minutes at 5000 rpm to separate the light phase ("oil") from the heavy phase ("gums").

The DAG content of the recovered oil was determined to contain 3.8%, an increase of 2.3 percent. The phospholipid profile obtained by P31-NMR analysis of the heavy phase confirmed the hydrolysis of the phosphatidyl groups to the corresponding lyso-groups, which is consistent with a PLA reaction. Very small amounts of "C" and "E" were detected, as well the "A". The PLA does not possess any significant PLC activity.

Example 13

PLA at neutral pH—50 grams of wet soybean gums, obtained from an industrial degumming centrifuge, were added to a 500 ml round bottom flask. 2 grams of Novozymes' Lecitase® (PLA1 lipase lot number LYN05007) were added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzyme were heated to 45° C. under continuous agitation. The system was maintained for eight hours. The apparatus was then disassembled and the hydrolyzed gums were collected. The gums were placed in a centrifuge tube and centrifuged for 15 minutes at 5000 rpm to separate the light phase ("oil") from the heavy phase ("gums"). The DAG content of the recovered oil was determined to contain 2.6 percent, an increase of only 1.1 percent DAG. The phospholipid profile showed all of the "original" gums were hydrolyzed, but a depressed amount of lyso- and phospho-derivatives were found in comparison to the control conditions in Example 12. This suggests that under the reaction conditions of this example, the PLA enzyme does not generate DAG, oil, or phospho species but does generate lyso-species and fatty acids.

Example 14

PLC and PLA at neutral pH-50 grams of wet soybean gums, obtained from an industrial degumming centrifuge, were added to a 500 ml round bottom flask. 10 grams of Verenium's Purifine™ (PLC lipase lot number 90BU004A1) and 2 grams of Novozymes' Lecitase® (PLA1 lipase lot number LYN05007) were added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzymes were heated to 45° C. under continuous agitation. The system was maintained for eight hours. The apparatus was then disassembled and the hydrolyzed gums were collected. The gums were placed in a centrifuge tube and centrifuged for 15 minutes at 5000 rpm to separate the light phase ("oil") from the heavy phase ("gums").

The DAG content of the recovered oil was determined to contain only 7.8 percent, compared to the 32.6% DAG content obtained when PLC was used alone. The phospholipid profile confirmed that all of the phosphatidyl groups where hydrolyzed to the phospho- and lyso-groups. The phospho-groups of "C", "E", and "A" were detected in roughly the same amount as was detected in Example 11, except that the amount of "I" was slightly depressed. The 1-PE was slightly depressed while l-PC and l-PA were both roughly twice the amount found in Example 11, but not a large increase. The amount of l-PI and l-PA where significantly higher than were found in Example 11, since PLA was also in the reaction matrix and converted the PI and PA to their lyso-forms.

The P-31 NMR analysis not only confirmed the PLC conversion of approximately the same amount of phospholipids to their phospho-groups as in the Control Example 11, but also confirmed that the remaining phosphatidyl groups were converted to their lyso-forms, indicating PLA conversion. This is a surprising result because the pH conditions were not optimum for PLA conversion. The amount of DAG present in the oil should have been roughly 33 percent, not 7.8 percent as was determined by HPLC analysis!

The P-31 NMR analysis not only confirmed the PLC conversion of approximately the same amount of phospholipids to their phospho-groups as in the Control Example 11, but also confirmed that the remaining phosphatidyl groups were converted to their lyso-forms by PLA. The amount of DAG present in the oil should have been roughly 33 percent, not 7.8 percent as was determined by HPLC analysis!

Table 7 summarizes the phospholipid profiles obtained by P31 NMR, with all numbers stated as weight percent of the heavy phases separated from the reaction mixtures of examples 11-15, showing the unreacted phosphatidyl moieties, the lyso-groups generated by PLA conversion, and the phospho groups generated by PLC conversion.

TABLE 7

| Example | PC | PE | PI | PA | l-PC | l-PE | l-PI | l-PA | "C" | "E" | "I" | "A" |
|---|---|---|---|---|---|---|---|---|---|---|---|---|
| Starting Material | 9.36 | 9.32 | 5.50 | 4.86 | 0.62 | 0.00 | 0.00 | 0.00 | 0.00 | 0.00 | 0.00 | 0.00 |
| 11 | 0.00 | 0.00 | 5.45 | 0.54 | 0.59 | 0.30 | 1.58 | 1.65 | 4.27 | 3.20 | 0.40 | 1.36 |
| 12 | 0.00 | 0.00 | 0.00 | 0.00 | 19.91 | 19.01 | 13.19 | 10.80 | 0.05 | 0.05 | 0.00 | 0.39 |
| 13 | 0.00 | 0.00 | 0.00 | 0.00 | 7.59 | 7.17 | 5.07 | 3.97 | 0.12 | 0.05 | 0.00 | 0.17 |
| 14 | 0.00 | 0.00 | 0.00 | 0.00 | 1.23 | 0.23 | 7.39 | 3.70 | 4.40 | 3.40 | 0.22 | 1.47 |
| 15 | 0.00 | 0.00 | 0.00 | 0.00 | 1.09 | 2.71 | 8.29 | 4.86 | 4.25 | 3.00 | 0.50 | 1.37 | the oil should have been roughly 33 percent, not 7.8 percent as was determined by HPLC analysis!

Example 15

PLC and PLA at pH 4.5—50 grams of wet soybean gums, obtained from an industrial degumming centrifuge, were added to a 500 ml round bottom flask. 2.0 grams of 50% w/w solution of citric acid was added and mixed for 5 minutes. Then 1.8 milliliters of 4 molar sodium hydroxide solution was added, and the mixture was mixed for an additional 5 minutes. The citric acid and caustic formed a weak buffer with a pH of 4.5. 10 grams of Verenium's Purifine™ (PLC lipase lot number 90BU004A1) and 2 grams of Novozymes' Lecitase® (PLAT lipase lot number LYN05007) were added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzymes were heated to 45° C. under continuous agitation. The system was maintained for eight hours. The apparatus was then disassembled and the hydrolyzed gums were collected. The gums were placed in a centrifuge tube and centrifuged for 15 minutes at 5000 rpm to separate the light phase ("oil") from the heavy phase ("gums").

The DAG content of the recovered oil was the same as in Example 14, 7.8 percent. The phospholipid profile confirmed that all of the phosphatidyl groups where completely hydrolyzed to the phospho- and lyso-groups as in Examples 12 through 14. The phospho-groups of "C", "E", "I" and "A" were detected in roughly the same amount as was detected in Example 11. l-PC and l-PE were significantly higher than were found in Example 11. Like Example 13, the amount of l-PI and l-PA were significantly higher than were found in Example 11, since PLA was also in the reaction matrix and converted the PI and PA to their lyso-forms. As in the degumming examples 1 through 10, the amount of DAG actually found was less than what had been expected based on the P-31 NMR analysis; suggesting that the DAG and FFA that were generated were consumed in the subsequent generation of TAG.

Table 8 below is a summary of the initial DAG, and Acid Value (AV) of the starting gums for each of examples 11-15 above, the theoretical amount of DAG and FFA that would have been present in the finished oil if all the phospholipids in the starting oil had reacted with the enzymes and the actual DAG present in the final oil. The final FFA was not measured because the FFA measurement procedure required more oil than was available from these experiments. In each of these examples, less DAG was found in the recovered oil than was expected, further supporting the conclusion that the DAG was consumed in the generation of TAG by the reaction of DAG with FFA.

TABLE 8

| Example | Starting Lecithin | | Enzyme Type | Theoretical Total | | Recovered Oil | |
|---|---|---|---|---|---|---|---|
| | DAG (%) | AV*** (%) | | DAG* (%) | FFA** (%) | DAG (%) | FFA**** (%) |
| 11 | 1.5 | 21 | PLC | 40.2 | 0.0 | 32.6 | — |
| 12 | 1.5 | 21 | PLA | 1.5 | 24.1 | 3.8 | — |
| 13 | 1.5 | 21 | PLA | 1.5 | 24.1 | 2.6 | — |
| 14 | 1.5 | 21 | PLC/PLA | 40.2 | 7.6 | 7.8 | — |
| 15 | 1.5 | 21 | PLC/PLA | 40.2 | 7.6 | 7.8 | — |

*Theoretical DAG only includes generation from phosphatidyl choline and phosphatidyl ethanolamine.
**Theoretical FFA includes the generation from all phospholipids when PLA is reacted. When PLC and PLA are reacted together, only the FFA from phosphatidyl serine, phosphatidyl inositol, and phosphatidic acid are calculated.
***The Acid Value (AV) is the number of milligrams of potassium hydroxide necessary to neutralize the acids in one gram of sample (1). AV is a representation of the titratable acidity contributed by both the phospholipids and the free fatty acids. (2).
****The FFA was not measured due to the large amount of sample required to perform the titration.

The following Example 16 is identical in terms of process steps to Example 15, other than being doubled in scale. The purpose of this Example was to perform a mass balance on the entire sample before and after the PLA/PLC enzyme reaction to verify the generation of triacylglycerols from the reaction byproducts of the PLA/PLC hydrolysis of the phospholipids.

Example 16

PLC and PLA at pH 4.5—100 grams of wet soybean gums, obtained from an industrial degumming centrifuge, were added to a 500 ml round bottom flask. 4.0 grams of 50% w/w solution of citric acid was added and mixed for 5 minutes. Then 3.6 milliliters of 4 molar sodium hydroxide solution was added, and the mixture was mixed for an additional 5 minutes. The citric acid and caustic formed a weak buffer with a pH of 4.5. 20 grams of Verenium's Purifine™ (PLC lipase lot number 90BU004A1) and 4 grams of Novozymes' Lecitase® (PLAT lipase lot number LYN05007) were added. The material was mixed with an overhead paddle mixer equipped with a stainless steel rounded paddle to fit the curvature of the flask at a rate of approximately 150 rpm. The flask was covered with Parafilm® to prevent evaporation of the water. The wet gums and enzymes were heated to 45° C. under continuous agitation. The system was maintained for eight hours. Samples of both the starting gums and the enzymatically treated mixture were analyzed "as is" for moisture, percent gums, and neutral oil content. Neutral oil content was measured by the method set forth in the Appendix below. The separated neutral oil was then analyzed for diacylglycerol content. The results are listed in Table 9.

TABLE 9

|  | Starting Gums | Enzyme Treated Gums |
|---|---|---|
| Moisture (%) | 24.0 | 32.7 |
| Percent Gums ("as is") | 55.8 | 27.3 |
| Percent Gums ("dry") | 73.4 | 41.4 |
| Percent Neutral Oil ("as is") | 20.2 | 38.7 |
| Percent Neutral Oil ("dry") | 26.5 | 58.6 |
| DAG (%) | 1.5 | 13.2 |

The starting wet gums analysis is typical for wet gums obtained from an industrial water degumming operation on soybean oil. Of the non-aqueous material in the sample, the gums were roughly 73 percent and the neutral oil was roughly 27 percent. The analysis of the "enzyme treated gums" from Example 16 demonstrates that a substantial portion of the phospholipids present were hydrolyzed by the PLA/PLC enzymes phospholipids, as shown by the decrease of gums from 73 to 41 percent, while the amount of triacylglycerols showed an increase from 26.5% to 58.6%. Theoretically, the amount of diacylglycerols expected to be generated by the process was 40.2%, but was found to be only of 13.2%. It is concluded that the combination of PLC and PLA enzymes utilized for oil degumming, purification, or modification of lecithins generates triacylglycerols, or oil.

There has been disclosed a method of generating triacylglycerols from phosphatidyl-containing oil gums by treating the gums with a combination of PLA and PLC enzymes, whereby the DAG by product of the PLC reaction and the FFA byproduct of the PLA reaction combine with one another in the presence of the enzymes to form new TAG molecules. The two different enzymes can be reacted with the gums either simultaneously or sequentially; when a sequential process is used, the enzymes can be added in either order. The reaction time of the enzymes with the gums can be on the order of about four hours or less, and can be as low as about thirty minutes. The enzymes having PLA activity can be selected from the group consisting of a phospholipase A1 enzyme and a phospholipase A2 enzyme. The PLA enzyme can be present in the reaction mixture in a concentration of about 2 ppm of active enzyme or less; or 1 ppm of active enzyme or less; or as low as 0.5 ppm of active enzyme or less. The enzymes having PLC activity can be selected from the group consisting of a phospholipase C enzyme and a phosphatidyl-inositol specific phospholipase C enzyme. The PLC enzyme can be present in the reaction mixture in a concentration of about 30 ppm of active enzyme or less; or 20 ppm of active enzyme or less; or as low as 10 ppm of active enzyme or less.

The enzyme reactions can be carried out at a temperature in the range of about 40-80° C., preferably in the range of about 40-60° C. The pH can be in the range of about 3-7. The enzyme reaction can be facilitated by shear mixing, preferably for about forty-five seconds or more when performed on a laboratory scale. It is expected that the time allotted for shear mixing will increase as the process is scaled up to industrial levels, as would be known to those skilled in the art. Also, acetone precipitation of the phosphorous containing material would allow the recovery of the generated oil; such a process is known in the art in the production of de-oiled lecithins.

While preferred embodiments of the invention have been set forth herein as known at the time of this application, other embodiments encompassing the inventive method will be readily apparent to those skilled in the art, and all such embodiments and their equivalent are intended to be covered by this application encompassed by the claims hereof.

APPENDIX

The following method was used to determine the neutral oil of the examples in this application.
Definition
This method determines the total neutral oil found in wet gums, lyso-gums, or crude oil soapstock.
Scope
Applicable to gums, lyso-gums, and soapstock.
Reference
A.O.C.S. Method G 5-40
A.O.C.S. Method Ca 2c-55
A.O.C.S. Method Ja 4-46
Apparatus
1. Graduated Cylinder—100 ml
2. Graduated Cylinder—50 ml
3. Graduated Cylinder—25 ml
4. Disposable Centrifuge Tubes—50 ml (Polypropylene)
5. Separatory Funnel—500 ml
6. Beaker—500 ml
7. Beaker—400 ml
8. Beaker—250 ml
9. Glass Stirring Rods
10. Centrifuge
11. Desiccator
12. Steam Bath
13. Oven—105° C.
Reagents
1. Aqueous potassium hydroxide (KOH)—14% by weight.
2. Sodium Chloride (NaCl)—Reagent grade.
3. Ethyl alcohol—SDA Formulas 30 and 3A are permitted, 50% by volume. Mix 10 volumes of 95% alcohol with 9 volumes of distilled water.
4. Ethyl alcohol—SDA Formulas 30 and 3A are permitted, 10% by volume. Mix 2 volumes of 95% alcohol with 17 volumes of distilled water.
5. Petroleum ether—ACS grade.
6. Acetone—ACS grade.
7. Deionized or distilled water
8. Nitrogen—clean and dry
Procedure
1. Perform % moisture on the sample immediately after the sample is pulled. Note: AOCS 2c-55, temperature is lowered to 105° C. due to foaming of soap samples at 130° C. Time is increased to 4 hours.
2. Mix sample thoroughly and weigh immediately.

3. Weigh 5 grams (to the nearest 0.0001 g) of sample into a previously weighed 50 ml disposable centrifuge tube. (Note: include the cap and beaker (for holding the centrifuge on scale)).

4. Add 35 ml of cold acetone (kept in an ice bath) to the sample and mix very well with a glass stir rod. Break up the lecithin precipitate with the glass rod. Note: The acetone will become bright yellow.

5. Cap the centrifuge tube.

6. Centrifuge the acetone for 5 minutes to separate the gums from the acetone.

7. Pour the acetone into a 250 ml beaker.

8. Repeat steps 4 through 7 four times.
   a. After the last extraction, remove the gums and place into a previously weighed disposable drying pan. Allow the excess acetone to evaporate.
   b. Place sample into a 105° C. draft oven overnight.
   c. Cool to room temperature in a desiccator and weigh the contents of the drying pan and sample.
   d. Calculate the percent gums in the original sample and on a dry basis.

9. Pour the acetone layer into a 500 ml separatory funnel ("A").

10. Add 50 ml of water to separatory funnel. Mix.

11. Add 50 ml of Petroleum Ether (P.E.). Mix.

12. Add a pinch of NaCl (~¼ table spoon of table salt) to the separatory funnel. Mix 13. Allow the two layers to separate. Remove the bottom layer (acetone/water), including any emulsion and add it to a new separatory funnel ("B-1"). DO NOT DISCARD THE P.E. LAYER.

14. Add 50 ml of Petroleum Ether (P.E.) to the acetone/water from step 13. Mix

15. Allow the two layers to separate. Remove the bottom layer (acetone/water), including any emulsion to a new separatory funnel ("B-2").

16. Add the Petroleum Ether layer to the original P.E. extract from step 13, separatory funnel "A".

17. Repeat steps 14 through 16 two times. The acetone/water layer may be added to a used funnel "B-1" from above. Once the last extraction is complete, you may discard the acetone/water layer.

18. Add 100 ml of 50% ethanol to the separatory funnel containing the P.E. Mix.

19. Add 10 ml of 14% KOH. Mix gently.

20. Add 50 ml of 50% ethanol to separatory funnel. Mix.

21. Allow the layers to completely separate. Do not allow the P.E. layer to remain in contact with the alcohol/KOH layer longer than 30 minutes. DO NOT DISCARD THE P.E. LAYER.

22. Remove the alcohol/KOH layer and place in a new separatory funnel.

23. Add 50 ml of P.E. to the separatory funnel containing the alcohol/KOH layer. Mix.

24. Allow layers to separate. Collect the alcohol/KOH layer into a new separatory funnel. Add the P.E. layer to the P.E. from step 21.

25. Repeat steps 23 and 24.

26. In the separatory funnel containing the P.E. Layers. Add 25 ml of 10% alcohol, shake vigorously. Allow the layers to separate. Remove the alcohol layer. Discard alcohol layer.

27. Repeat step 26 twice. To the third "washing" (alcohol layer), add two drops of phenolphthalein to determine if the layer is neutral. If the layer turns pink, repeat step 26.

28. Draw the P.E. layer into a tared beaker that has been previously dried and cooled in a desiccator. Evaporate the P.E. on a steam bath under a gentle stream of nitrogen.

29. Once the P.E. has been removed, Place beaker in an oven at 105° C. for 30 minutes.

30. Cool in a desiccator to ambient temperature and weigh.

31. Repeat until constant weight is attained. (A constant weight is attained when the loss (or gain) in weight does not exceed 0.1% in successive 30 minute drying periods.)

Calculation

Neutral Oil, % (as is)=Mass of Neutral Oil/Mass of Sample×100

Neutral Oil, % (dry basis)={Mass of Neutral Oil/Mass of Sample}/{100-Percent Moisture}×100

Gums, % (as is)=Mass of Dried Gums/Mass of Sample×100

Gums, % (dry basis)={Mass of Dried Gums/Mass of Sample}{100-Percent Moisture}×100

What is claimed is:

1. A method of generating triacylglycerols comprising
   (a) providing an oil composition containing a quantity of oil gums, wherein the gums comprise phospholipids,
   (b) treating the oil composition with one or more enzymes having PLA activity to generate free fatty acids,
   (c) treating the oil composition with one or more enzymes having PLC activity to generate diacylglycerols,
   (d) reacting the fatty acids with the diacylglycerols in the presence of at least one of the enzymes having PLA or PLC activity, thereby forming triacylglycerols.

2. The method of claim 1, wherein steps (b) and (c) occur substantially simultaneously.

3. The method of claim 1, wherein step (b) occurs before step (c).

4. The method of claim 1, wherein step (c) occurs before step (b).

5. The method of claim 1, wherein the total duration of the treating of the enzymes with the oil composition in steps (b) and (c) and the reacting in step (d) is no more than about four hours.

6. The method of claim 5, wherein the total duration of the treating of the enzymes with the oil composition in steps (b) and (c) and the reacting in step (d) is about thirty minutes.

7. The method of claim 1, wherein the one or more enzymes having PLA activity are selected from the group consisting of a phospholipase A1 enzyme and a phospholipase A2 enzyme.

8. The method of claim 1, wherein the one or more enzymes having PLC activity are selected from the group consisting of a phospholipase C enzyme and a phosphatidylinositol specific phospholipase C enzyme.

9. The method of claim 1, wherein the treating of steps (b) or (c) or the reacting of step (d) comprises treating or reacting at a pH of about 8 or less.

10. The method of claim 9, wherein the pH is about 3-7.

11. The method of claim 1, wherein the treating of the enzymes with the oil composition in steps (b) and (c) and the reacting in step (d) occurs at a temperature of about 40-80° C.

12. The method of claim 11, wherein the treating of the enzymes with the oil composition in steps (b) and (c) and the reacting in step (d) occurs at a temperature of about 40-60° C.

13. The method of claim 1, wherein the oil composition comprises a crude oil.

14. The method of claim 1, wherein in steps (c) or (d), the PLC enzyme is present in a quantity of about 30 ppm of active enzyme or less.

15. The method of claim 14, wherein the PLC enzyme is present in a quantity of about 20 ppm of active enzyme or less.

16. The method of claim 15, wherein the PLC enzyme is present in a quantity of about 10 ppm of active enzyme or less.

17. The method of claim 1, wherein in steps (b) or (d), the PLA enzyme is present in a quantity of about 2 ppm of active enzyme or less.

18. The method of claim 17, wherein the PLA enzyme is present in a quantity of about 1 ppm of active enzyme or less.

19. The method of claim 18, wherein the PLA enzyme is present in a quantity of about 0.5 ppm of active enzyme or less.

20. The method of claim 1, wherein the treating of steps (b) or (c) comprise shear mixing the oil composition and the respective PLA or PLC enzymes to obtain a mixture.

21. The method of claim 20, wherein the shear mixing continues for a duration of at least 45 seconds.

22. The method of claim 20, wherein the treating of steps (b) or (c) further comprises adding a quantity of water to the mixture.

23. The method of claim 22, wherein the quantity of water is at least about 1.5% by weight of the mixture.

24. The method of claim 23, wherein the quantity of water is at least about 3.0% by weight of the mixture.

25. The method of claim 24, wherein the quantity of water is at least about 4.5% by weight of the mixture.

* * * * *